United States Patent [19]

McRoberts et al.

[11] Patent Number: 5,547,466
[45] Date of Patent: Aug. 20, 1996

[54] MALE GENITALIA SUPPORT

[75] Inventors: Samuel J. McRoberts, Palm Beach Gardens; Lee Kvarnberg, Jupiter, both of Fla.

[73] Assignee: Male Pouch, Inc., Tequesta, Fla.

[21] Appl. No.: 419,467

[22] Filed: Apr. 10, 1995

[51] Int. Cl.$^6$ ........................................ A61F 5/40
[52] U.S. Cl. ........................ 602/70; 602/73; 2/2; 2/403
[58] Field of Search ............................ 602/70, 72, 73; 2/2, 403

[56] References Cited

U.S. PATENT DOCUMENTS

| | | | |
|---|---|---|---|
| 908,533 | 1/1909 | Zuckriegel | 602/73 X |
| 1,019,501 | 3/1912 | Love et al. | 602/70 X |
| 4,122,849 | 10/1978 | Dietz | 602/70 |
| 4,141,357 | 2/1979 | Dietz | 602/70 |
| 5,029,345 | 7/1991 | Angheluta et al. | 602/70 X |

FOREIGN PATENT DOCUMENTS 221903  5/1910  Germany ................................ 602/70

Primary Examiner—Richard J. Apley
Assistant Examiner—Kim M. Lee
Attorney, Agent, or Firm—Thomas E. Coverstone

[57] ABSTRACT

A male genitalia support has a posterior testicular strap portion extending from a waist band portion. The posterior testicular strap portion is designed to be positioned behind the scrotum and testicles to provide support to the wearer's cremaster muscles and spermatic cords. The support is made of a generally unyielding material so that a constant, non-variable amount of support is provided to the wearer. A receptacle, made of an air-permeable material, for accepting the male's genitalia may be attached to the support.

26 Claims, 4 Drawing Sheets

MALE GENITALIA SUPPORT

TECHNICAL FIELD OF THE INVENTION

This invention relates to support devices for male genitalia, and more particularly, to an undergarment to be used as a support device for male genitalia.

BACKGROUND OF THE INVENTION

Support garments for male genitalia are well known. The support garments of the prior art typically have a cup shaped support fastened to the male body by either an elastic waist band or an elastic waist band in combination with leg straps.

U.S. Pat. No. 2,888,014 issued to Dougharty discloses a Suspensory that has a pocket that is supported by three straps. Two straps encircle the legs and the third strap encircles the waist. An absorbent pad is used with the suspensory when the wearer has urinary infections.

U.S. Pat. No. 2,798,484 issued to Boudreaux discloses a suspensory that includes a wire supported pouch that provides support without the use of understraps, or straps around the wearer's thighs.

U.S. Pat. No. 3,225,761 issued to Swensen discloses a male suspensory comprising a pouch with side panels, the side panels are secured to an elastic belt. A folded front edge of the side panels forms a front opening and folded rear edge of the side panels defines a rear opening. The elastic belt maintains the spaced relationship of the openings, as well as the support for the suspensory as the elastic belt is placed around the wearer's waist.

U.S. Pat. No. 3,314,422 issued to Phillips discloses a contoured pouch that may be molded from plastic or foam rubber. The cup may be incorporated into a male garment as the crotch portion, or it may be provided with a fastening means for fastening the pouch to the male body.

U.S. Pat. No. 4,141,357 issued to Dietz discloses a cup supporter that utilizes a spherical shaped pouch with an elastic band having two attachment straps to fasten the cup supporter to an undergarment. The amount of length and tension of the elastic band is adjusted for the comfort of the wearer. The elastic band is located on the anterior side of the lower torso region.

Also, U.S. Pat. No. 4,122,849 issued to Dietz discloses yet another cup supporter with an elastic waist band. This cup supporter provides shape to the wearer's genitalia region by shaping the male genitalia while worn. The pouch is made from a laminate sheet of foam rubber. Elastic is sewn to the top edge of the pouch, which is attached to an elastic strap that is to be placed around the waist of the wearer. The elastic is to be adjusted for the comfort of the wearer and to adjust the amount of support given by the supporter. The cup's shape changes as the elastic band at the top edge of the cup is stretched.

The prior art supporters attempt to provide a comfortable and lightweight supporter that provides continuous and steady support to the male genitalia. However, it is evident when reviewing the prior art that the designs are insufficient in the amount of continuous and non-variable support given to the male genitalia, and more particularly, to the support of the scrotum and the testicles to prevent excessive strain upon the cremaster muscle and the spermatic cords.

Such a support of the scrotum and testicles is desired after minor surgery, such as a vasectomy, or during and after a case of epididymitis, where support of the cremaster muscles and the spermatic cords aids in the patient's healing process and raises the patient's comfort level during these events.

The U.S. Pat. No. 4,122,849 issued to Dietz attempts to provide a scrotum support, however, Dietz is directed more towards an all-around solution to support and shaping. The cup-shaped pouch design, and more importantly, the design "template" shown in FIG. 3, does not teach a line of support needed behind the scrotum and testicle area to support the cremaster muscles and spermatic cords.

In addition, the cup pouch is made from a foam rubber. Foam rubber is not a material that would allow the passage of air for the ventilation of the wearer's genitalia area. Therefore, the wearer would become hot and perspiration would occur. The wearer would become uncomfortable and would be prone to the growth of fungi (most particularly, tinea cruris, or jock itch) and bacterial infections at the genitalia region. The growth of fungi and bacteria in the genitalia area should be avoided, especially after surgery in the genitalia area. The surgical incision after surgery should have an adequate and proper amount of ventilation of fresh air to promote healing. The foam rubber cup supporters of the prior art lack the capability to provide the proper amount of ventilation after a surgical procedure in the genitalia region.

Further, Dietz (4,122,849) discloses the use of an elastic strap at the top edge of the pouch and the cup's shape changes as the elastic is stretched. Therefore, as the wearer of the supporter would move around in his daily activities, and as the wearer's lower torso moves, the cup's shape would be constantly changing in shape and vary in the amount of support given to the wearer's scrotum and testicles. This design would certainly be uncomfortable for the wearer after surgery or after an illness; it would also be uncomfortable to an every day user absent the surgery or illness.

Therefore, what is needed is a support for male genitalia that emphasizes support at the scrotum for the testicles, and more particularly, a support for the testicular muscles and cords.

DISCLOSURE OF THE INVENTION

It is, therefore, an object of the present invention to provide a male genitalia support that is lightweight and comfortable to wear.

It is also an object of the present invention to provide a male genitalia support that provides for the ventilation of air at the genitalia region while being worn.

It is also an object of the present invention to provide a male genitalia support that has an adjustable waist band.

It is also an object of the present invention to provide a male genitalia support that supports the scrotum and testicles to prevent excessive strain upon the cremaster muscles and the spermatic cords, or generally, the testicular muscles and cords.

It is also an object of present invention to provide a male genitalia support that may be used after surgery, such as a vasectomy, herniorrhaphy, or during and after an illness, such as a case of epididymitis or hydrocele, where the supporter aids in the patient's healing process and raises the patient's comfort level during these events.

It is also an object of the present invention to provide a male genitalia support that provides a constant, non-variable amount of support to the posterior side of the scrotum and testicles, and more particularly, to the cremaster muscles and the spermatic cords.

According to the present invention, a male genitalia support has a posterior testicular strap portion extending from a waist band portion. The posterior testicular strap portion is designed to be positioned behind the scrotum and testicles. The posterior testicular strap portion is an extension of the waist band portion, so that the waist band portion provides support to the testicular strap portion while the supporter is worn. A lateral strap portion extends laterally from the waist band portion across the anterior side of the lower torso area of the wearer. A receptacle for accepting the male's genitalia may be attached to the support, the receptacle extends from the posterior testicular strap portion to the lateral strap portion. The receptacle accepts and houses the wearer's scrotum, testicles, and penis.

In combination, the waist band portion and the testicular strap portion establish a line of support for the scrotum and testicles. The waist band portion and the testicular strap portion are made of a material that is generally unyielding while experiencing tensile stresses. Therefore, the line of support provides a constant, non-variable amount of support to the cremaster muscles and the spermatic cords, or generally, the testicular muscle and cords.

The waist band portion has a fastening means for fastening the waist band portion to the posterior testicular strap portion after the waist band portion is positioned around the waist of the wearer. The waist band portion has an adjusting means for adjusting the length of the waist band portion, and ultimately, the amount of support given by the testicular strap portion to the scrotum and the testicles. The waist band portion may be adjustable to accommodate wearers of a variety of waist sizes. The supporter may also be incorporated into an undergarment for a more conventional look and feel.

The receptacle is made from a lightweight and air-permeable fabric, such as cotton or silk. The fabric is constructed to create a receptacle for the scrotum, testicles, and penis.

The foregoing and other advantages of the present invention will become more apparent from the following description and accompanying drawings.

BEST MODE FOR CARRYING OUT THE INVENTION

Figure 1:
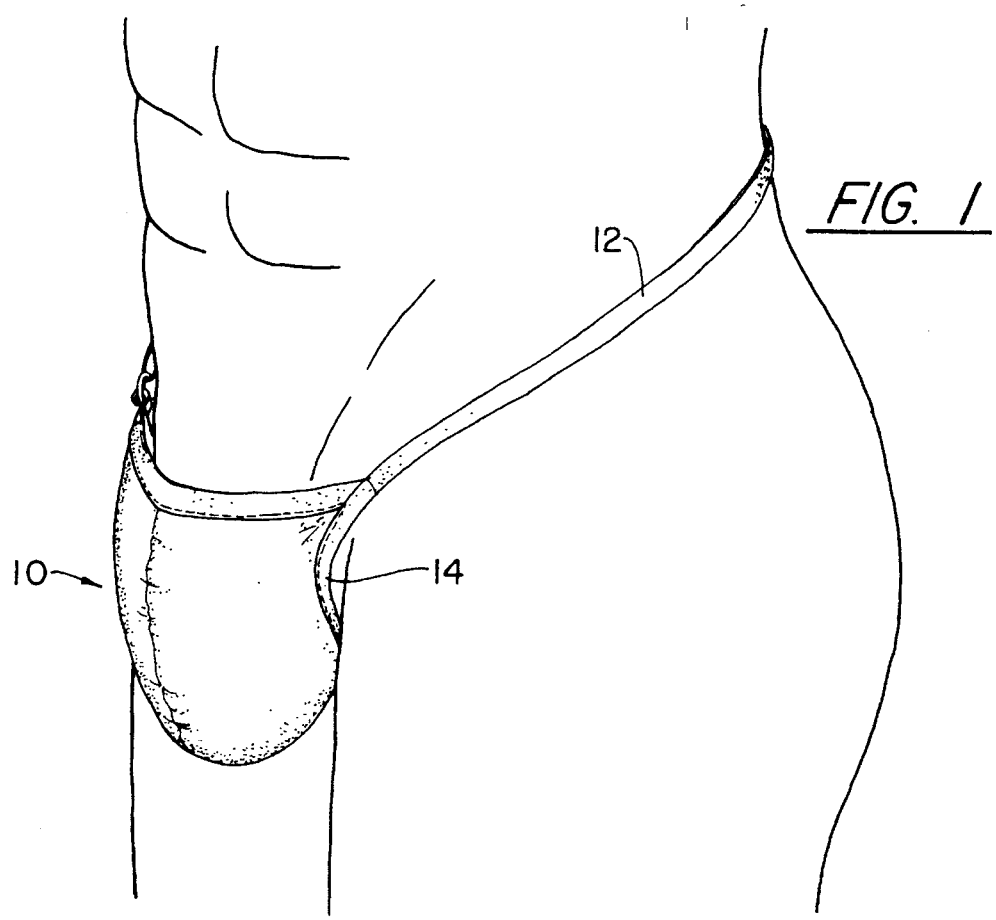
FIG. 1 is a front perspective view of a male genitalia support of the present invention, as worn by the wearer.

According to the present invention, and as shown in FIG. 1, a male genitalia support 10 is provided to give support to the wearer's scrotum and testicles.

The scrotum is a pouch of skin lying below the pubic symphysis and in front of the upper parts of the thighs. The scrotum contains the testes, or both testicles, and the lowest parts of the spermatic cords.

Below the skin of the scrotum is a layer of involuntary muscle, the dartos, which alters the appearance of the scrotum. The cremaster muscle is a thin muscle layer covering the spermatic cord through which sperm travels. The function of the cremaster muscles is to pull the testicles toward the body in response to cold temperature or stimulation to the nerves.

Beneath the dartos muscle are layers of fascia continuous with those forming the coverings of each of the two spermatic cords, which suspend the testes within the scrotum and contain each ductus deferens, the testicular blood and lymph vessels, the artery to the cremaster muscles, the artery to each ductus deferens, the genital branch of the genitofemoral nerve, and the testicular network of nerves. Therefore, each cord is made up of arteries, veins, lymphatics, nerves, and the excretory duct of the testicles. The spermatic cord is the structure by which each testicle is attached to the body. The left spermatic cord is usually longer than the right, thus the left testis usually hangs lower than the right.

The testes each have an epididymis, which is a long tightly coiled tube that ends in a single tube called the vas deferens, which empties into an ejaculatory duct in the posterior urethra, which carries sperm from the testicle to the tip of the penis. Epididymitis is an inflammation of the epididymis. Epididymitis may result from urinary infection, venereal disease, prostate surgery or trauma.

In regards to the present invention, the cremaster muscles and spermatic cords, and more generally, the muscles, cords, and ducts that attach and connect the testicles to the pelvis area and the body in general, are referred to in a general sense as testicular muscles and cords.

Figure 2:
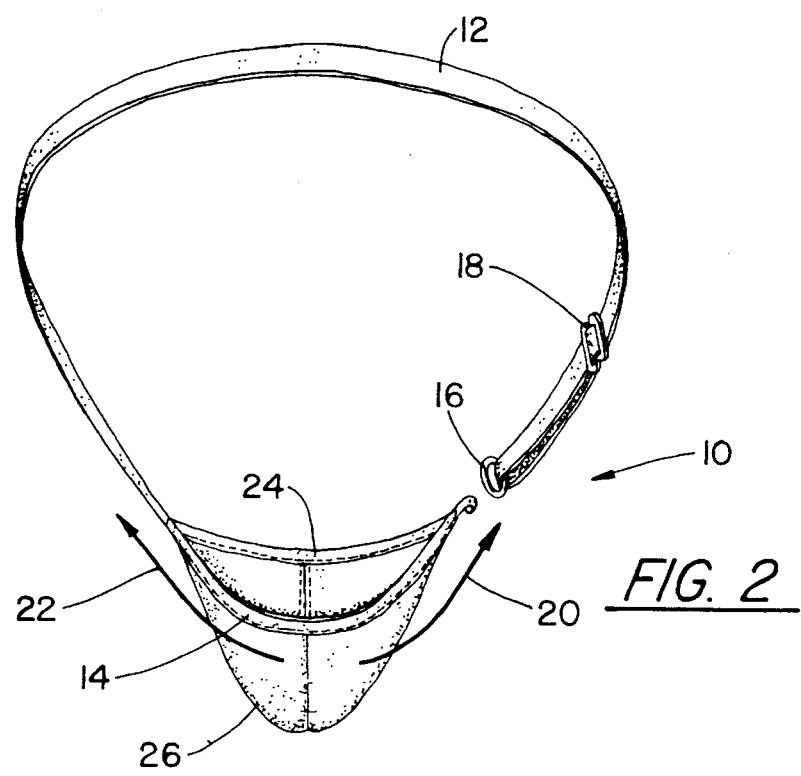
FIG. 2 is a rear perspective view of the male genitalia support of the present invention.

As shown in FIG. 1, the male genitalia support 10 has a waist band portion 12 that is to be placed around the waist of the male wearer. Referring now to FIG. 2, the male genitalia support 10 also has a posterior testicular strap portion 14 extending from the waist band portion 12. A fastening means 16 may connect the waist band portion 12 to the posterior testicular strap portion 14 for the ease of wearer. Without limiting the scope of the present invention, the preferred embodiment shows a single hook and loop faster 16. Alternative fastening means are discussed below.

The waist band portion 12 may include an adjustment means 18 so that the waist band portion 12 may be adjusted to accommodate a variety of waist sizes, or to accommodate for the waist line dimensional changes of one particular wearer. The adjustment means 18 also adjusts the amount of support and lift given to the testicles provided by the posterior testicular strap portion 14. The amount of support and lift provided to the testicles may be adjusted according the wearer's needs and comfort level. The adjustment means 18 is a conventional slide well known in the art, where one end of the waist band portion 12 is fixedly attached to the adjustment means 18 so that the overall length of the waist band portion 12 may be shortened or lengthened by sliding the adjustment means in relation to the waist band portion itself.

When the posterior testicular strap portion 14 is placed on the posterior side of the scrotum and testicles and the waist band portion 12 is placed around the wearer, support or lift is provided along the posterior testicular strap 14, as generally shown by arrows 20 and 22.

The male genitalia support 10 may include a lateral strap portion 24, connecting to the posterior testicular strap 14. When placed on the wearer, the lateral strap portion 24 extends across the anterior lower torso area of the wearer. Minimal, if any, load is experienced at the lateral strap portion 24. The functional purpose for the lateral strap portion 24 is so that a receptacle 26 may be attached to the posterior testicular strap 14 and to the lateral strap portion 24. The receptacle 26 accepts and houses the wearer's scrotum, testicles, and penis. The receptacle 26 provides only minor and secondary support to the testicles; the primary lifting and support of the testicles is provided by the posterior testicular strap 14.

Figure 3:
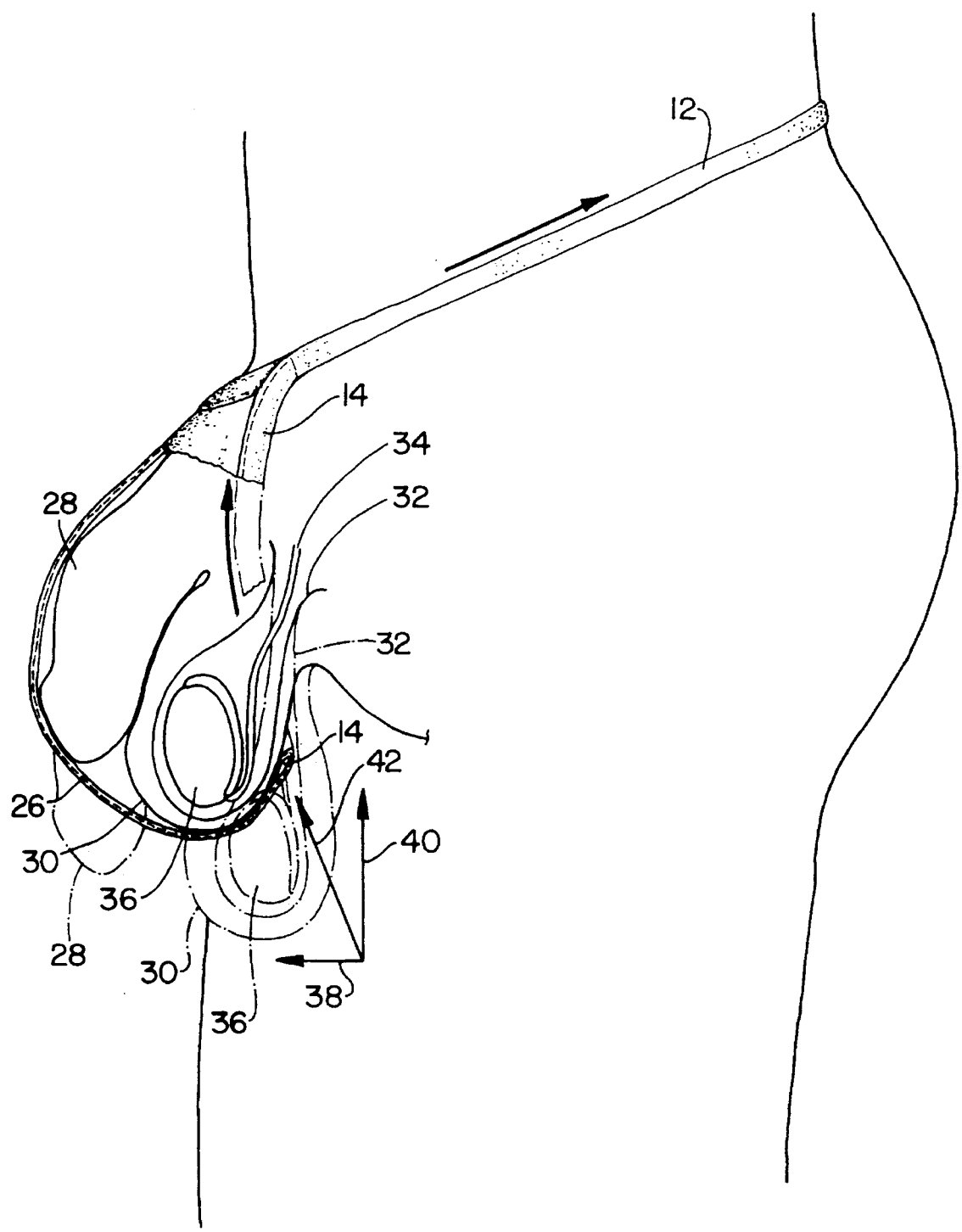
FIG. 3 is cross sectional view of the male genitalia support of the present invention showing the area of support given to the male genitalia of the wearer.

Referring now to FIG. 3, the male genitalia support 10 is shown in a cross sectional view as worn by the wearer. The wearer's penis 28 is shown housed in the receptacle 26, as is the wearer's scrotum 30 and testis 36. The cremaster muscle 32 is shown surrounding the spermatic cord 34; the cremaster muscle 32 supports the testes 36. The posterior testicular strap portion 14 is shown on the posterior side of the scrotum 30 and testis 36.

As the posterior testicular strap portion 14 is lifted by the waist band portion 12, a horizontal force vector 38 and a larger vertical force vector 40 combine to give the resultant force vector 42. The resultant force vector, or line of support 42 lifts and supports the testicular muscles and cords of the wearer, relieving the testicular muscles and cords from tensile forces and strain.

The waist band portion 12 and posterior testicular strap 14 are made of a generally unyielding material so that the amount of support given to the testicular muscles and cords is a constant and non-variable lifting support. As the wearer walks, sits, or stands, the support given to the testicular muscles and cords is non-variable. This non-variable amount of support, together with the comfort given to the wearer, combine to be key advantages of the male genitalia support 10 over the prior art. The use of the term non-variable support is not to be confused with adjustable support. The male genitalia support 10 has an adjustment means 18 to adjust the amount of support given to the testicular muscles and cords, and once the amount of support is adjusted to the wearer's comfort level, the amount of support is non-variable as the wearer walks, sits, stands, etcetera.

The male genitalia support 10 is particularly useful after surgery to the male genitalia area, such as a vasectomy or herniorrhaphy, or after an illness such as epididymitis or hydrocele, or after an injury to the male genitalia area. Support of the testicular muscles and cords aids in the patient's healing process and raises the patient's comfort level during these events.

The use of the male genitalia support 10, however, does not need to be limited to post-surgery, injury, or illness. Some people find the look of boxers and briefs to be unappealing or thongs to be uncomfortable. The male genitalia support 10 provides an alternative undergarment for the male, while providing support and having an aesthetic appearance. Therefore, the support 10 may be worn as an everyday article of clothing.

As another alternative, the male genitalia support 10 may be sewn into ordinary undergarments to the give the support 10 a more conventional look and feel. The male genitalia support 10 may also simply be worn underneath ordinary undergarments, such as boxer shorts or briefs.

To reduce the opportunity for bacteria to grow at the male genitalia area, particularly after surgery in that area, the receptacle 26 is made from an air-permeable material, such as cotton or silk, that allows the passage of air for the ventilation of the wearer's genitalia area. Ventilation of the area will help to reduce temperature and perspiration in the genitalia area. The use of the air-permeable material will increase the wearer's comfort level and reduce the possibility of the growth of fungi (most particularly, tinea cruris, or jock itch). The air-permeable material will help to ventilate the surgical incision after surgery and the ventilation of fresh air will promote healing of the incision.

The fastening means 16 of the present invention may be of a variety of designs, and without limiting the scope of the present invention, three alternative fastening means are described below.

Figure 4:
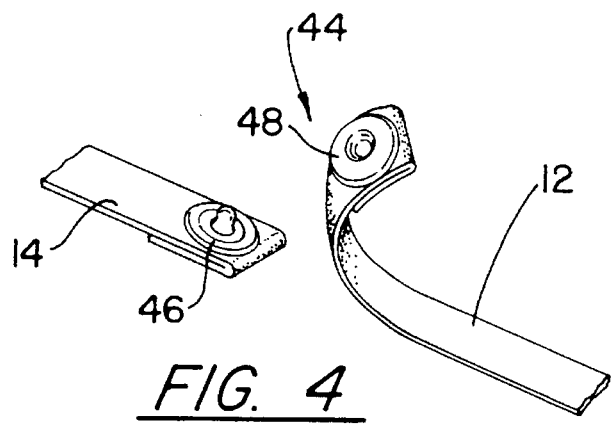
FIG. 4 is a perspective view of an alternative fastening means for the male genitalia support of the present invention.

As shown in FIG. 4, an alternative fastening means 44 has a fixed male snap portion 46 that would be attached to the posterior testicular strap 14 and a female snap portion 48 that would be attached to the waist band portion 12. The female snap portion 48 accepts and fastens to the male snap portion 46.

Figure 5:
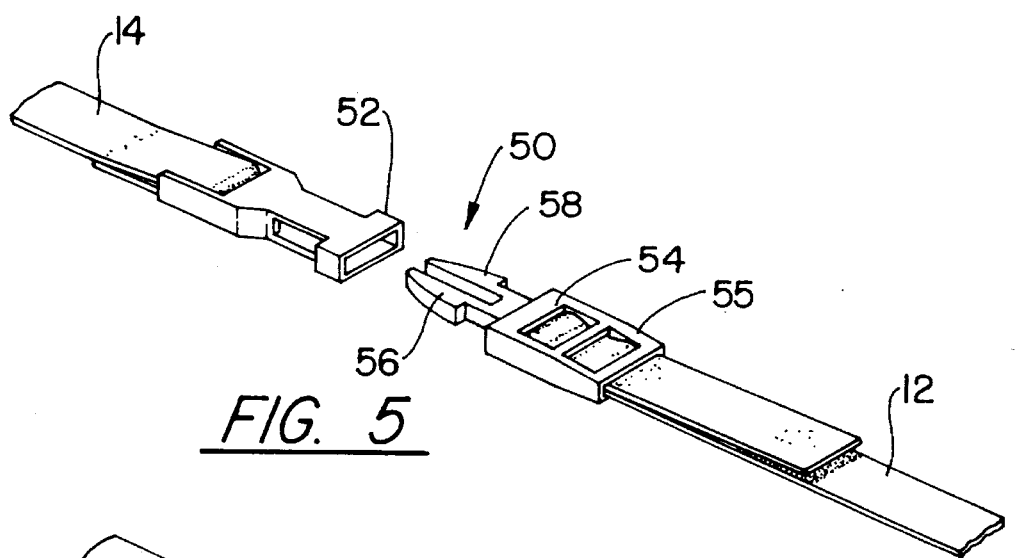
FIG. 5 is perspective view of an alternative fastening means for the male genitalia support of the present invention.

As shown in FIG. 5, an alternative fastening means 50 has a female snap portion 52 that would be attached to the posterior testicular strap 14 and a male snap portion 54 that would be attached to the waist band portion 12. The male snap portion 54 may include an adjustable slide 55 for adjusting the amount of support given by the support 10. The male snap portion 54 has a first prong 56 and a second prong 58. The female snap portion 52 accepts the prongs 56 and 58 and fastens to the male snap portion 54.

Figure 6:
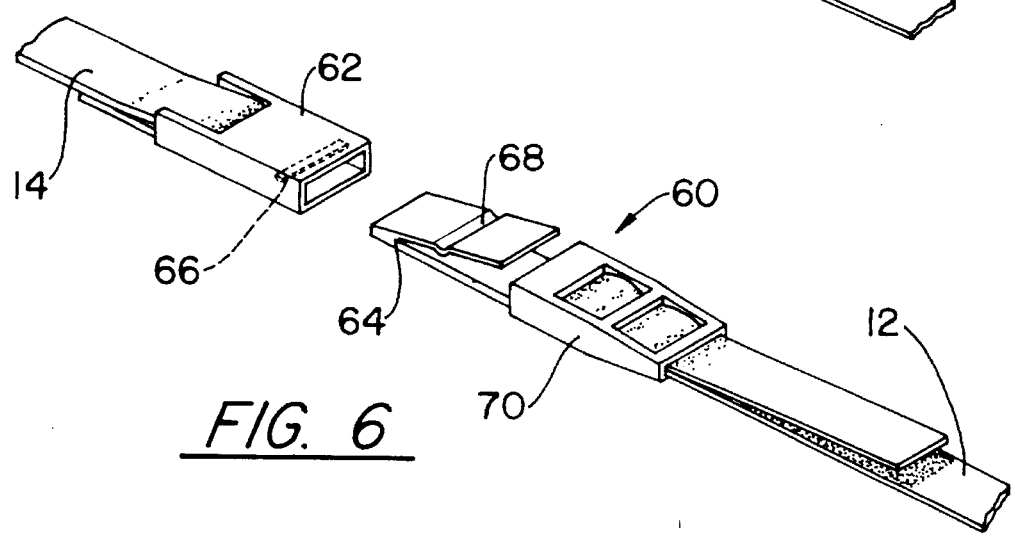
FIG. 6 is perspective view of yet another alternative fastening means for the male genitalia support of the present invention.

As shown in FIG. 6, an alternative fastening means 60 has a female snap portion 62 and a male snap portion 64. The female snap portion 62 has an internal ridge 66 and the male snap portion 64 has a groove 68 that matches the size and shape of the ridge 66. The male snap portion 64 may include an adjustable slide 70 for adjusting the amount of support given by the support 10. The female snap portion 62 accepts and fastens to the male snap portion 64, while the internal ridge 66 positions itself in the groove 68.

Figure 7:
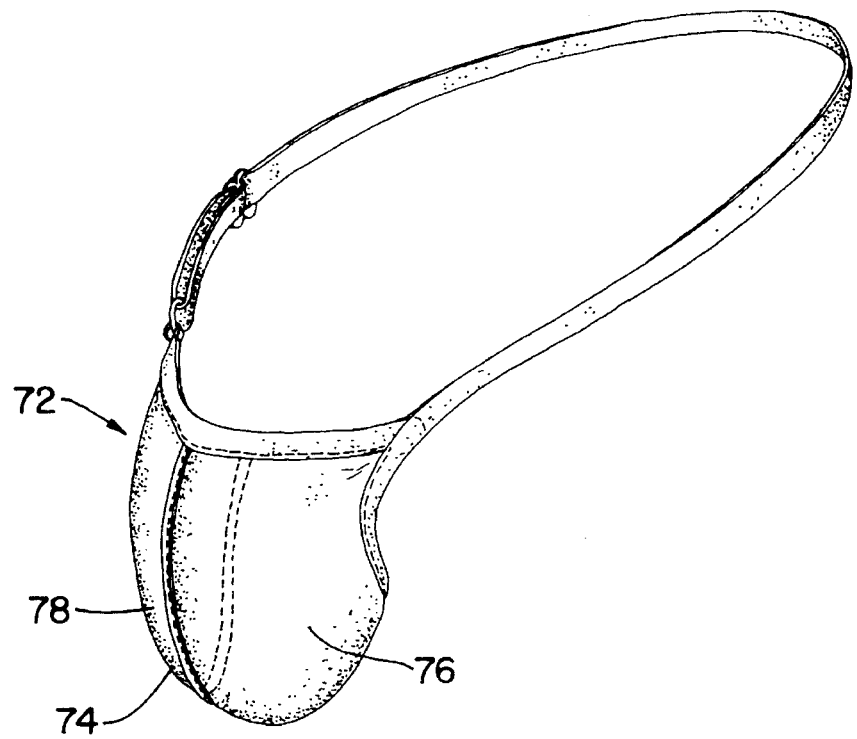
FIG. 7 is a separate embodiment of the present invention, wherein a receptacle has an opening for the penis.

As shown in FIG. 7, a separate embodiment of the present invention is disclosed, which is similar to the above embodiment except that a male genitalia support 72 has a receptacle 74 that has two overlapping flaps 76 and 78. The flaps 76 and 78 may be pulled apart easily by the wearer so that the support 72 has an opening for the wearer's penis to facilitate urination. This embodiment of the male genitalia support 72 would provide a continuous, non-variable amount of support for the wearer's testicular muscles and cords, even while the wearer performs necessary bodily functions.

Figure 8:
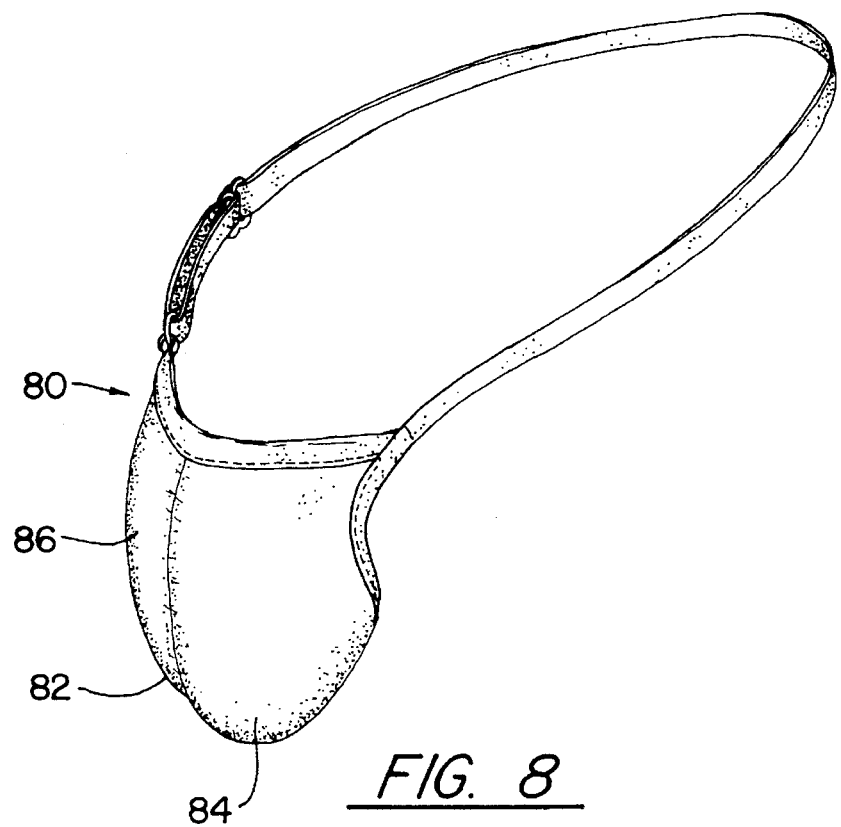
FIG. 8 is yet another embodiment of the present invention, wherein a receptacle has one two compartments with one compartment being larger than the other.

As shown in FIG. 8, a separate embodiment of the present invention is disclosed. A male genitalia support 80 has a receptacle 82 that has a left compartment 84 and a right compartment 86. The left compartment 84 is shown to be slightly larger in relation to the right compartment 86 to accommodate for the predominately naturally occurring lower hanging left testicle of the wearer. Of course, the receptacle may have a larger right compartment in relation to the left compartment, or the compartments 84 and 86 may be equal, depending on the wearer's anatomical requirements.

The male genitalia support of the present invention and as disclosed provides a constant and non-variable line of support to the testicular muscles and cords, relieving the testicular muscles and cords from excessive strain and tensile stress when the wearer requires extra support, such as after surgery, injury, or an illness. The male genitalia support of the present invention is also comfortable to wear while providing support on a daily basis.

Although this invention has been shown and described with respect to a detailed embodiment, those skilled in the art will understand that various changes in form and detail may be made without departing from the spirit and scope of the claimed invention.

We claim:

1. A male genitalia support, comprising:

a posterior testicular strap portion adapted to be positioned on the posterior side of the wearer's scrotum and testicles when worn;

a waist band portion that is adapted to be positioned around the waist of the wearer, the posterior testicular strap portion extending from the waist band portion, the posterior testicular strap portion and the waist band portion being made from a generally unyielding material so that the posterior testicular strap portion relieves stress from and provides support to the wearer's testicular muscles and cords.

2. The male genitalia support of claim 1, wherein the posterior testicular strap portion is made from a generally unyielding material so that a constant and non-variable amount of support is given to the testicular muscles and cords.

3. The male genitalia support of claim 1, wherein the waist band portion has means for fastening so that the waist band portion may be placed around the wearer's waist and fastened.

4. The male genitalia support of claim 1, wherein the waist band portion has means for adjusting the length of the waist band portion to accommodate different waist sizes and to adjust the amount of support given by the posterior testicular strap portion.

5. The male genitalia support of claim 1, further comprising:

a receptacle attached to the posterior testicular strap portion, the receptacle accepting and housing the wearer's scrotum, testicles, and penis.

6. The male genitalia support of claim 5, wherein the receptacle is made of an air-permeable material so that ventilation is allowed through the receptacle.

7. The male genitalia support of claim 5, further comprising:

the receptacle having a left compartment and a right compartment, one of the compartments being larger than the other compartment to accommodate for anatomical differences in testicular size, length, and shape.

8. The male genitalia support of claim 5, wherein the support is sewn into an existing conventional undergarment.

9. The male genitalia support of claim 5, wherein the receptacle further comprises two overlapping flaps that may be easily pulled apart by the wearer so that support has an opening for the wearer's penis to facilitate bodily functions.

10. The male genitalia support of claim 5, further comprising:

a lateral strap portion extending laterally from the waist band portion across the wearer's lower torso area.

11. The male genitalia support of claim 10, wherein the receptacle is attached to the posterior testicular strap portion and to the lateral strap portion.

12. A male genitalia support for relieving stress on and providing support to the cremasteric muscles and the spermatic cords, comprising:

a posterior testicular strap portion adapted to be positioned on the posterior side of the wearer's scrotum and testicles;

a waist band portion adapted to be worn around the waist of the wearer, the posterior testicular strap portion extending from the waist band portion;

the waist band portion having means for fastening so that the waist band portion may be placed around the wearer's waist and fastened;

the waist band portion having means for adjusting the length of the waist band portion to accommodate different waist sizes and to adjust the amount of support given by the posterior testicular strap portion;

the posterior testicular strap portion and the waist band portion being made from a generally unyielding material so that a constant and non-variable amount of support is given to the testicular muscles and cords.

13. The male genitalia support of claim 12, further comprising:

a receptacle attached to the posterior testicular strap portion, the receptacle being made of an air-permeable material so that ventilation is allowed through the receptacle, the receptacle accepting and housing the wearer∝s scrotum, testicles, and penis.

14. The male genitalia support of claim 13, wherein the receptacle further comprises two overlapping flaps that may be easily pulled apart by the wearer so that the support has an opening for the wearer's penis to facilitate bodily functions.

15. A male genitalia support, comprising:

a posterior testicular strap portion and a waist band portion, the posterior testicular strap portion extending from the waist band portion, the posterior testicular strap portion and the waist band portion being made from a generally unyielding material, the waist band portion having means for fastening so that the male genitalia support may be fastened around the wearer's waist, so that when the posterior testicular strap portion is positioned on the posterior side of the wearer's scrotum and testicles, and the waist band portion is positioned around the wearer's waist, the male genitalia support relieves the wearer's testicular muscles and cords from tensile stress.

16. The male genitalia support of claim 15, the waist band portion further comprising means for adjusting the length of the waist band portion, so that the amount of support given by the male genitalia support to the wearer's testicular muscles and cords may be adjusted.

17. The male genitalia support of claim 15, wherein the posterior testicular strap portion and the waist band portion are made from a generally unyielding material so that a constant and non-variable amount of support is given to the wearer's testicular muscles and cords.

18. The male genitalia support of claim 17, the support providing a line of support given by the posterior testicular strap portion to the wearer's testicular muscles and cords.

19. The male genitalia support of claim 18, the line of support further comprising:

a horizontal force vector and a vertical force vector, the force vectors combining to result in a resultant force vector defining the line of support.

20. The male genitalia support of claim 15, further comprising:

a receptacle attached to the posterior testicular strap portion, the receptacle housing the wearer's scrotum, testicles, and penis.

21. The male genitalia support of claim 20, wherein the receptacle is made of an air-permeable material so that ventilation is allowed through the receptacle.

22. The male genitalia support of claim 20, further comprising:

a lateral strap portion extending laterally from the waist band portion across the wearer's lower torso area.

23. The male genitalia support of claim 22, wherein the receptacle is attached to the posterior testicular strap portion and to the lateral strap portion.

24. The male genitalia support of claim 20, further comprising:

the receptacle having a left compartment and a right compartment, one of the compartments being larger than the other compartment to accommodate for anatomical differences in testicular size, length, and shape.

25. The male genitalia support of claim 20, wherein the support is sewn into an existing conventional undergarment.

26. The male genitalia support of claim 20, wherein the receptacle further comprises two overlapping flaps that may be pulled apart by the wearer so that the support has an opening for the wearer's penis to facilitate bodily functions.

* * * * *